United States Patent [19]

Zimmerman et al.

[11] Patent Number: 5,607,741

[45] Date of Patent: *Mar. 4, 1997

[54] PHENOLIC ACID SULFATE ESTERS FOR PREVENTION OF MARINE BIOFOULING

[75] Inventors: Richard C. Zimmerman, Pacific Grove, Calif.; Randall S. Alberte, Arlington, Va.; James S. Todd, Walla Walla, Wash.; Phillip Crews, Santa Cruz, Calif.

[73] Assignees: ARCH Development Corporation, Chicago, Ill.; The Regents of the University of California, Oakland, Calif.

[ * ] Notice: The term of this patent shall not extend beyond the expiration date of Pat. No. 5,384,176.

[21] Appl. No.: 351,624

[22] Filed: Dec. 8, 1994

Related U.S. Application Data

[63] Continuation of Ser. No. 989,274, Dec. 11, 1992, Pat. No. 5,384,176.

[51] Int. Cl.$^6$ .................................................. B32B 9/04
[52] U.S. Cl. ........................ 428/68; 428/411.1; 428/543; 428/907; 422/6; 558/20; 558/37
[58] Field of Search ................................ 428/68, 411.1, 428/543, 907; 422/6; 558/20, 37

[56] References Cited

U.S. PATENT DOCUMENTS

| | | |
|---|---|---|
| 3,589,860 | 6/1971 | Foroulis . |
| 4,297,803 | 11/1981 | Saito ............................................. 43/7 |
| 4,774,080 | 9/1988 | Yamamori et al. ........................ 424/78 |
| 4,910,234 | 3/1990 | Yamamori et al. ...................... 523/122 |
| 4,918,147 | 4/1990 | Yamamori et al. ...................... 525/386 |
| 5,248,221 | 9/1993 | Gerhart et al. .......................... 405/216 |
| 5,252,630 | 10/1993 | Gerhart et al. .......................... 523/122 |
| 5,259,701 | 11/1993 | Gerhart et al. .......................... 405/216 |

OTHER PUBLICATIONS

"Epibiosis of Marine Algae and Benthic Invertebrates: Natural Products Chemistry and Other Mechanisms Inhibiting Settlement and Overgrowth," Davis et al., Bioorganic Marine Chemistry, vol. 3, 1989.

"Light Adaptation and the Role of Autotrophic Epiphytes in Primary Production of the Temperate Seagrass, *Zostera Marina* L" Mazzella et al., J. Exp. Mar. Biol. Ecol. 1986 vol. 100, pp. 165–180.

"Control of Microbial Growth and of Amphipod Grazing by Water–Soluble Compounds from Leaves of *Zostera marina*" Harrison, Paul G., Marine Biology, 1982.

"Seasonal Variation in Phenolic Content of Eelgrass Shoots," Harrison et al., Aquatic Botany, 35 (1989) pp. 409–413.

"Epiphytic bacterial production on *Zostera marina*" Kirchman, et al., Marine Ecology—Progress Series, vol. 15: 117–123, 1984.

"The Antifouling Activity of Natural and Synthetic Phenolic Acid Sulphate Esters," Todd et al., Phytochemistry, vol. 34, No. 2, pp. 401–404, 1993.

"Sargassum Tannin, An Antibiotic Which Retards Fouling," Sieburth et al., Nature, Oct. 2, 1965, pp. 52–53.

*Primary Examiner*—William A. Krynski
*Assistant Examiner*—Marie R. Yamnitzky
*Attorney, Agent, or Firm*—Reinhart, Boerner, Van Deuren, Norris & Rieselbach, s.c.

[57] ABSTRACT p-Sulfoxy cinnamic acid isolated from methanolic extracts of the eelgrass *Zostera marina* having significant antifouling aquatic properties. p-Sulfoxy cinnamic acid was synthesized in the laboratory from p-coumaric acid, and antifouling activity was identical to the natural compound in laboratory bioassays. In addition, sulfate esters of other phenolic acids showed similar antifouling activity, suggesting that the sulfate ester was responsible for the antifouling effect.

10 Claims, 5 Drawing Sheets

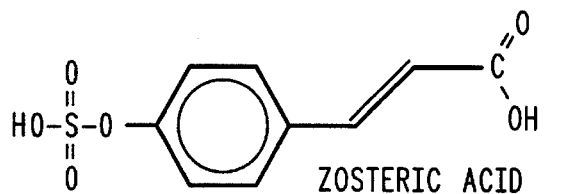
Fig. 1A
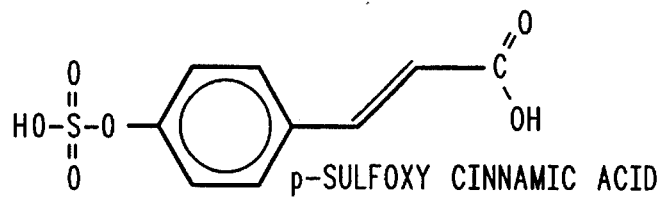
Fig. 1B
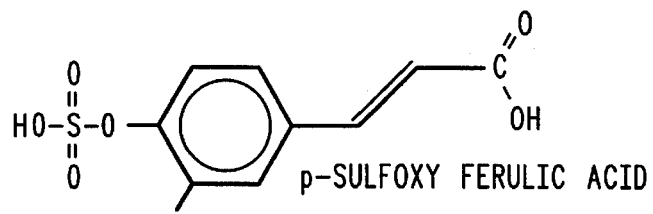
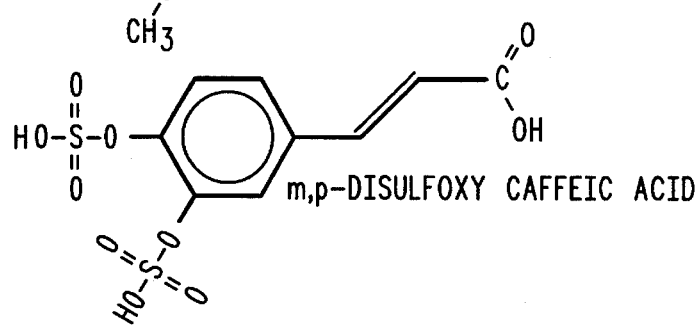
Fig. 1C
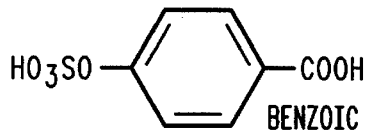
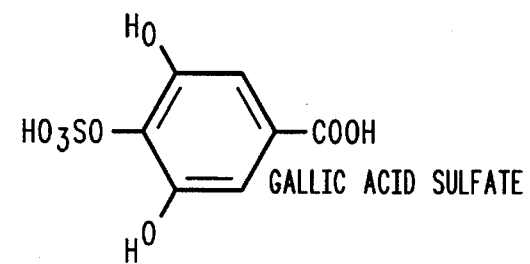
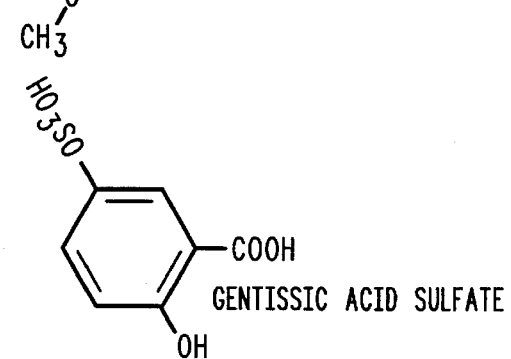
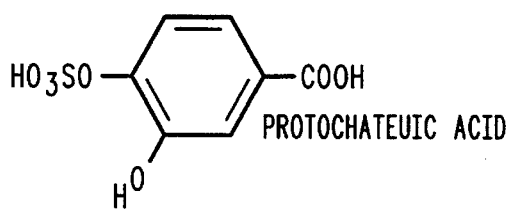

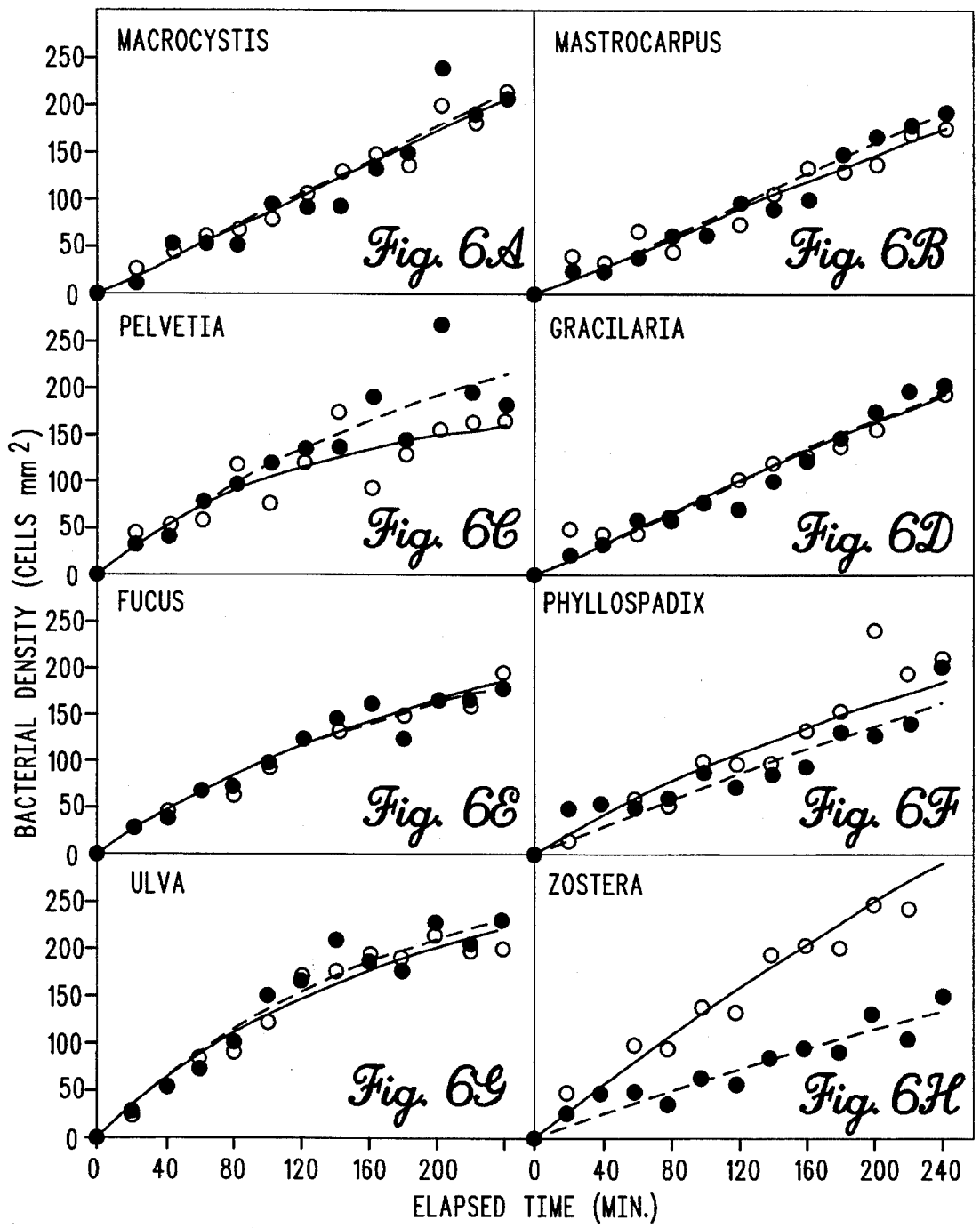

PHENOLIC ACID SULFATE ESTERS FOR PREVENTION OF MARINE BIOFOULING

The U.S. Government has rights in this invention pursuant to Contract No. N00014-88-K-0455 between the Office of Naval Research and the University of Chicago.

This is a continuation of application Ser. No. 07/989,274 filed on Dec. 11, 1992, now U.S. Pat. No. 5,384,176.

The control of biofouling on artificial surfaces is a significant problem for structures in contact with the marine environment. Subsequent to the removal of enviromentally hazardous organo-tin compounds from antifouling paints, control of biofouling accumulation has become the single most expensive maintenance problem incurred by the U.S. Navy for ship operations. In addition, the recent introduction of zebra mussels threatens to become a major biofouling hazard in freshwater environments throughout the United States, particularly in the Great Lakes region. Thus, the quest for an environmentally-safe and effective antifouling formulation for structures continues to be the subject of much research and development. We have prepared a compound (zosteric acid) that has significant antifouling properties yet has proven to be non-toxic when tested against a wide range of living organisms.

Organisms have evolved a variety of mechanisms that prevent fouling of their surfaces. Some may reduce the accumulation of fouling agents by physical means, including the sloughing of the outer tissue layer, and/or the production of an external surface that minimizes bioadhesion. The production of secondary metabolites that are capable of deterring potential fouling organisms and predators is relatively common among marine organisms. However, the chemical species employed to effectuate this type of protective mechanism are as diverse as the organisms manufacturing them. Known compounds include elemental vanadium and inorganic acids, as well as a variety of organic compounds including saponins, terpenes and phenolic acids (Davis et al. 1989). Although the modest antifouling properties of water soluble phenolic acids were acknowledged in the 19th Century, practical exploitation of these compounds has been minimal due to their low effectiveness.

Eelgrass is a source for a number of phenolic acids and derivatives which include antifouling agents. Several sulfonated flavones and a host of non-sulfonated phenolic acids have been isolated from eelgrass tissue, some of which have been shown to have anti-biological activity. Crude aqueous extracts containing phenolic acids, in particular, have been found to have anti-microbial properties. It has been speculated that these compounds may be significant ecologically in preventing microbial infections, grazing and biofouling. The seasonal peaks in soluble phenolic acid abundance, however, coincides with maximum biofouling abundance, which suggests that phenolics are ineffective in preventing the accumulation of the biofouling load on eelgrass leaves.

It is therefore an object of the invention to provide an improved antifouling composition.

It is another object of the invention to provide a novel use of a naturally occurring chemical compound.

It is a further object of the invention to provide an improved method of protecting structures in contact with marine environments from fouling.

It is an additional object of the invention to provide a novel structural article of manufacture resistant to marine fouling.

It is still another object of the invention to provide an improved antifouling compound which also is non-toxic.

It is yet another object of the invention to provide a novel method of disrupting bonding of marine organisms to a structure in contact with a marine environment.

It is still an additional object of the invention to provide an improved method of isolating zosteric acid under acidic solution conditions.

It is also another object of the invention to provide a novel method of use of sulfate esters of phenolic acid as marine antifouling compositions.

These and other objects will become apparent from the Detailed Description and from the Brief Description of the Drawings provided hereinbelow:

BRIEF DESCRIPTION OF THE DRAWINGS

FIG. 1A illustrates the chemical structure of naturally occurring zosteric acid; FIG. 1B shows phenolic acid sulfate esters synthesized in the laboratory; and FIG. 1C illustrates alternate phenolic acid sulfate esters;

FIGS. 6A (Macrocystis), 6B (Mastrocarpus), 6C (Pelvetia), 6D (Gracilaria), 6E (Fucus), 6F (Phyllospadix), 6G (Ulva), and 6H (Zostera) show bacterial density assays as a function of time performed with methanol extracts prepared from a variety of marine macrophytes. Open circles are control slide measurements.

DETAILED DESCRIPTION OF THE PREFERRED EMBODIMENTS

Zosteric acid was isolated from eelgrass by a microbial attachment assay through a series of chromatographic separations (Sephadex and HPLC). The purified agent was identified through $^{13}$C-NMR, $^1$H-NMR and high resolution fast atom bombardment mass spectrometry (HRFAMBS) as a sulfate ester derivative of cinnamic acid, p-sulfoxy cinnamic acid (FIG. 1A), (zosteric acid). The compound hydrolyzes under acidic conditions.

In order to verify that zosteric acid was indeed responsible for the antifouling property of the eelgrass extract, p-sulfoxy cinnamic acid was synthesized in the laboratory from chlorosulfonic acid and p-coumaric acid in pyridine. The mixture was extracted with ethanol, water and methanol and purified by HPLC. The product structure was verified by NMR and HRFAMBS examination.

The relatively simple structure of zosteric acid suggested that the sulfate group was responsible for the antifouling activity. To test the hypothetical role of the sulfate group in biofouling activity, other analogs (FIG. 1B) were prepared as above, using different phenolic acid precursors in the reaction sequence. Yields from this reaction were about 63% for all compounds. Other synthetic analogs shown in FIG. 1C also are included within the scope of this invention. The illustrated synthetic analogs include benzoic acid sulfate, vanillic acid sulfate, gentissic acid sulfate, gallic acid sulfate and protocatechuic acid. Variations on these fundamental compounds involve lengthening the carboxyl tail to control the rate of dissolution of the compound from a coating on a marine structure.

Figure 2A:
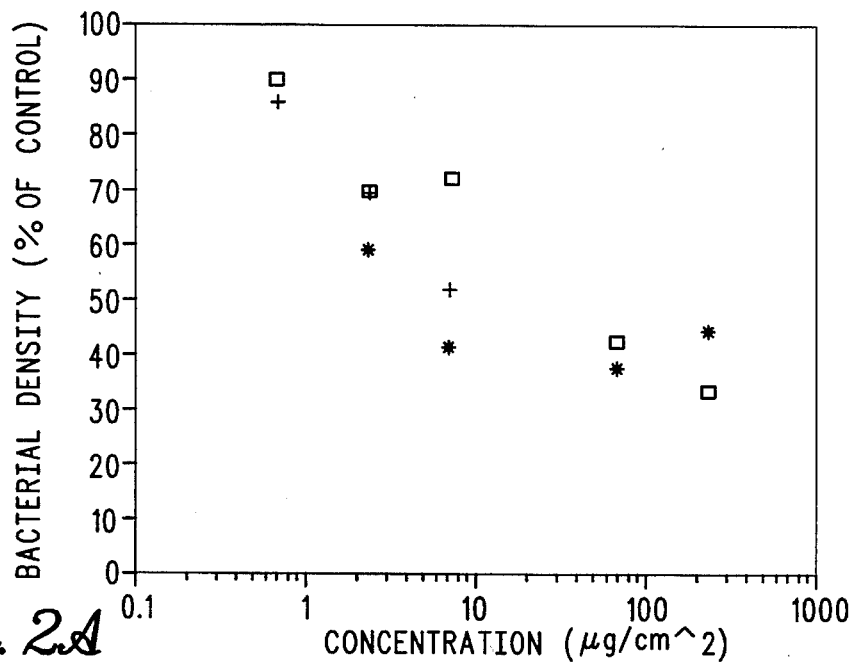
FIG. 2A shows bacterial density on glass slides as a function of concentration for different phenolic acid sulfates.
Figure 2B:
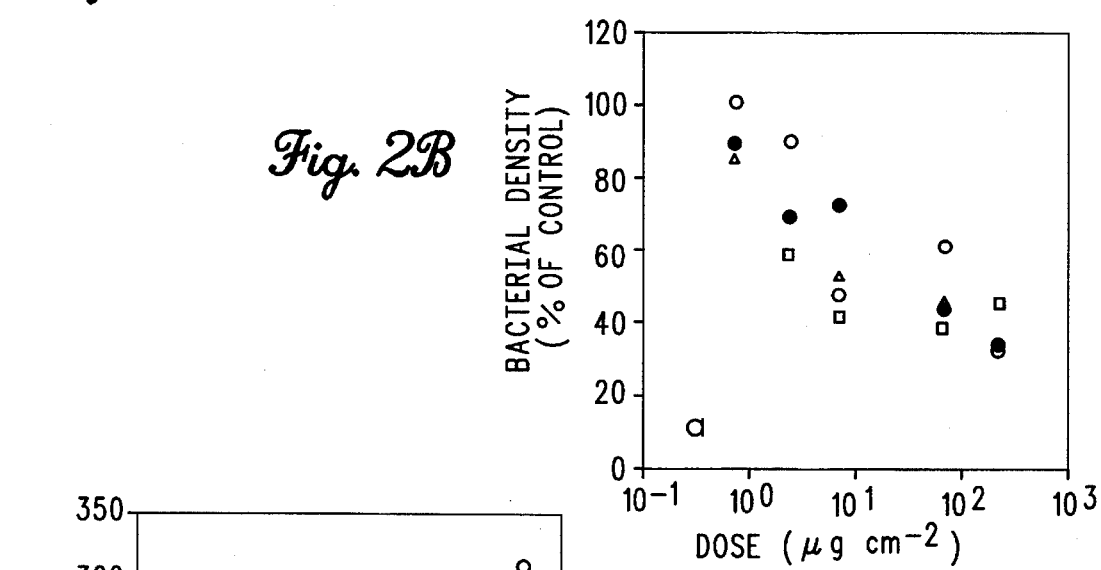
FIG. 2B shows antifouling dose response of natural zosteric acid (full circles); synthetic p. (sulfoxy) cinnamic acid (open circles); p-(sulfoxy) ferulic acid (open triangles), and (disulfoxy) caffeic acid (open squares) all relative to control slides against Acinetobacter sp.
Figure 2C:
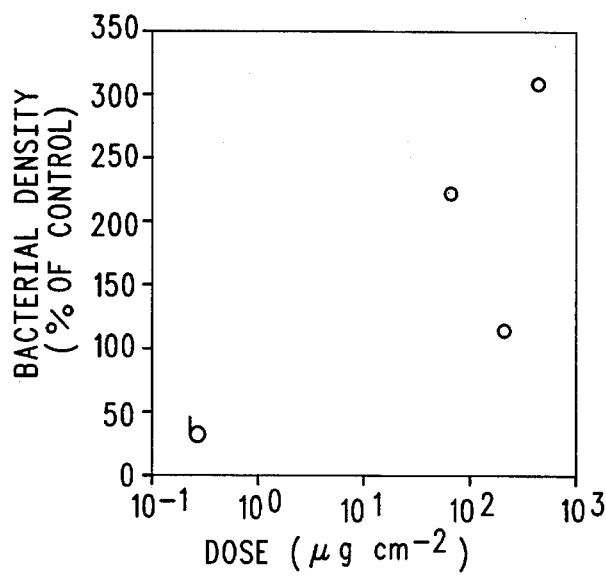
FIG. 2C illustrates the antifouling dose response curve ferulic acid (open circles)

Dose effectiveness of zosteric acid and the synthesized sulfate esters were evaluated in the laboratory using a microbial attachment assay. The ability of each individual compound to inhibit attachment of bacteria to glass slides was tested over a concentration range spanning four orders of magnitude. Based on these tests, purified zosteric acid was sufficiently effective against attachment to conclude that it is the primary agent responsible for the antifouling properties of the eelgrass extract (see FIG. 2). It also had sufficient activity to be considered as an agent for incorporation into antifouling coatings. The synthetic sulfate esters were as effective as natural zosteric acid in preventing bacterial attachment, making exploitation of natural eelgrass populations unnecessary for the production of zosteric acid in industrial quantities.

In contrast with natural zosteric acid, the simple phenolic acid precursors were ineffective over the same concentration range and in fact appear to have attracted bacteria to the glass slides in higher density than the controls in some cases. Without limiting other inventions described herein, this is believed to show that the presence of the sulfate ester is principally responsible for the antifouling properties of zosteric acid. The addition of a second sulfate ester (in the case of caffeic acid disulfate), however, did not increase the antifouling strength of the compound. The precise mode of action in producing the antifouling response remains undetermined; however, it should be noted that the extracellular polysaccharides produced by marine organisms are highly sulfated, and these sulfate esters play an important role in polymerization (i.e. glue/gel formation). Thus, without limiting the invention, zosteric acid could be operating at the atomic level by blocking sulfate-binding surface sensors, or by inhibiting the polymerization of the extracellular glue.

Figure 3:
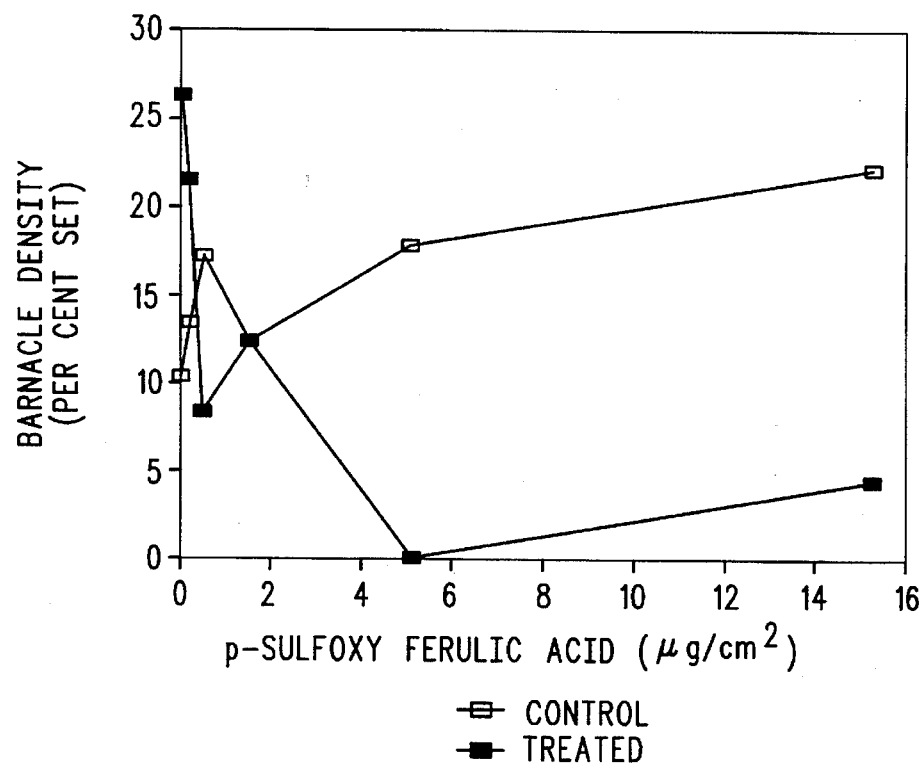
FIG. 3 illustrates barnacle density versus concentration of p-sulfoxy ferulic acid.

In addition to the bacterial assays described above, the dose-effectiveness of ferulic acid sulfate (FAS) was tested using a barnacle attachment assay. The IC-50 dose in the barnacle assay was similar to the results from the bacterial assay, suggesting a similar mode of action (see FIG. 3). In these tests, barnacles stopped swimming when exposed to the active agent, but quickly recovered when transferred to clean seawater, suggesting, as with the bacteria, that attachment was prevented by a mechanism other than acute toxicity.

Figure 4:
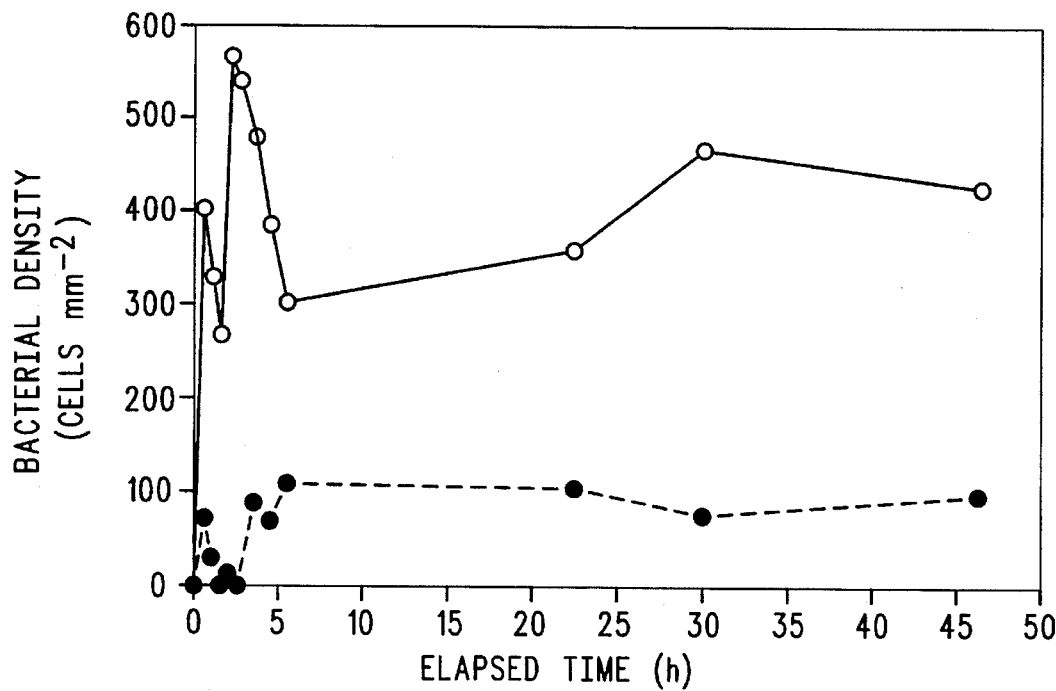
FIG. 4 shows time versus bacterial density on a glass slide treated with eelgrass extract and another slide separately treated with methanol solvent.

Short tests (<7d) were performed using crude eelgrass extract painted onto glass slides and ceramic tiles to see if laboratory results could be duplicated in the field. Treated slides accumulated significantly fewer bacteria than controls for 48 h (see FIG. 4). For both treatments, the initial colonization phase occurred within the first 5 h, after which populations remained stable for the next 45 h.

Figure 5A:
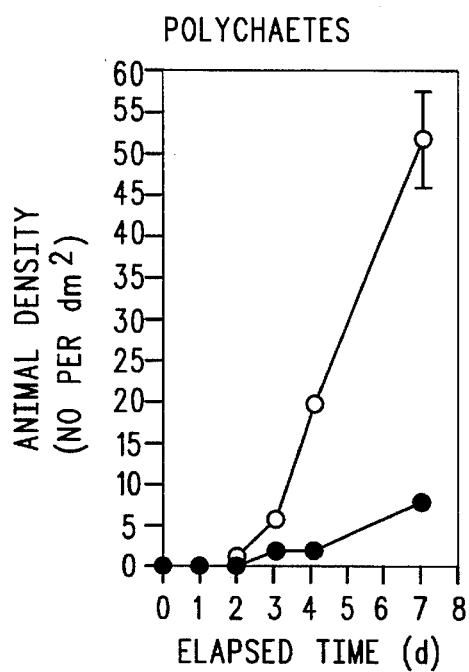
FIGS. 5A (Polychaetes), 5B (Colonial Tunicates), and 5C (Solitary Tunicates) illustrate densities of various organisms on ceramic tiles treated with methanol (open circles) and crude eelgrass extract (filled or dark circles)
Figure 5B:
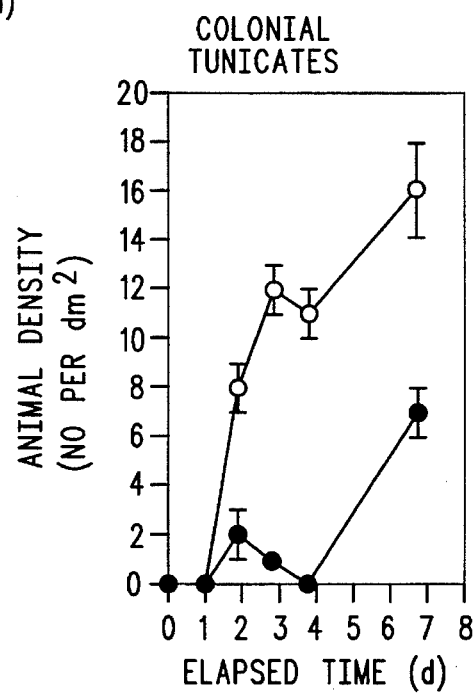
Figure 5C:
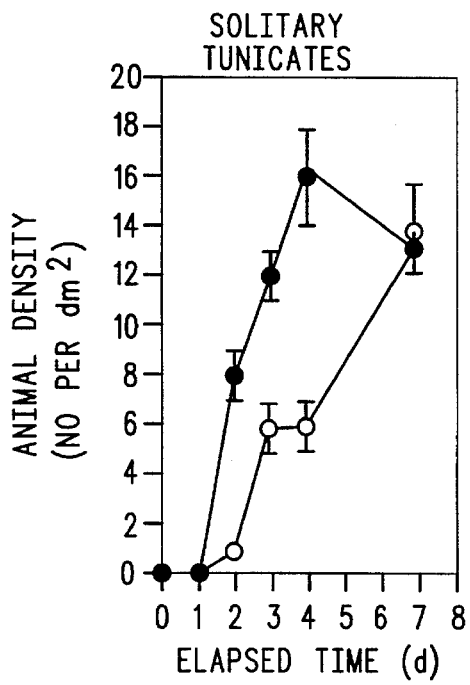

The crude extract was also capable of inhibiting the attachment of spirorbid polychaetes and colonial tunicates to ceramic tiles placed into the temperate environment of Moss Landing Harbor for as long as seven days (see FIG. 5). The extract was ineffective, however, against solitary tunicates. No barnacles settled on any of the plates during the course of this experiment.

In another form of the invention, methanolic extracts were prepared from freshly collected tissue of other macrophytes to determine whether the antifouling property of the eelgrass extract had its counterpart in other macrophytes. Representative species of red, brown and green algae, as well as another seagrass (Phyllospadix sp.) were included in this survey. A fresh extract of Z. marina was also prepared for comparative purposes. Bacterial attachment was inhibited by the eelgrass extract as shown previously, but not by any of the other specimens tested (FIG. 6). Thus Z. marina may be somewhat unique among marine plants with regard to the chemistry of antifouling defense. Furthermore, sulfate esters of phenolic acids do not appear to be widely distributed among disparate marine taxa, even though many of these species contain numerous phenolic compounds.

The following non limiting examples illustrate various aspects of the invention.

EXAMPLE I

Emergent shoots of the seagrass Zostera marina L. were collected by SCUBA divers from a subtidal bed 5–7 meters deep near Del Monte Beach, in Monterey Bay, Calif. (36° 30' 40" N, 121° 52' 30" W) in March (dry weight 575 g) and October (dry weight 1700 g) 1990.

The combined dry residue from three MeOH extractions (20°) of freshly dried ground eelgrass leaves was extracted with $H_2O$ prior to being partitioned between hexanes and 10% aq. MeOH; the MeOH phase was then diluted to 40% aq. MeOH and extracted with $CH_2Cl_2$. Bioassays of these fractions indicated antifouling activity was principally localized in the $H_2O$ extract. Lyophilization of the aqueous extract gave a hygroscopic solid that was separated batchwise into three colored bands on a Sephadex LH-20 column (42 cm ×3.2 cm OD, MeOH). The bioactivity was concentrated in the yellow band, which was identified as zosteric acid (1) after removal of inorganic salts and other impurities by HPLC. Quantitative estimates were not calculated from the March collection because preliminary experiments were performed with various fractions that resulted in acid decomposition of the zosteric acid (1). The October collection, however, yielded 66 mg of zosteric acid (1) from 1700 g dry biomass.

Final purification of all phenolic acid sulfates (natural and synthetic) was carried out by HPLC [Regis ODS irregular column, 25 cm ×10 mm ID; RI detector; 90% aq. MeOH solvent (100% $H_2O$ for 5–7); 1000 psi]. TLC $R_f$ values [silica gel; BuOH—HOAC—$H_2O$ (4:1:1); UV detection]: subspecimen 1 (0.63) and other analogs yielded values from (0.29)–(0.83).

EXAMPLE II

Frosted ends (4.5 cm² area) of glass microscope slides were treated with candidate fractions or purified compounds dissolved in MeOH and challenged against a clone of Acinetobacter sp. (a fouling marine bacterium isolated from the surface of eelgrass leaves). Control slides were treated with MeOH solvent only. Slides were placed into 50 ml screw-cap plastic tubes containing 30 ml of sterile, 0.2 μm-filtered seawater (FSW) and an inoculum of bacteria from a log-phase liquid culture (final bacterial concentration was ca. $10^6$ cells $ml^{-1}$). Tubes were capped and placed horizontally on a rotary shaker with the treated surface facing down. Slides were removed at 20 minute intervals, stained with Hoechst (#2287, Sigma Co.) and cell densities in the frosted regions were enumerated with the aid of epifluorescence microscopy (1000×). Attached bacterial densities on treated slides were normalized to control slides at each time point. Mean density (relative to MeOH control)

was calculated for each concentration from all data in the four hour time series.

Barnacle attachment assays were performed in plastic petri dishes treated with an analog of subspecimen 1 and control solvent (MeOH). Dishes were then filled with FSW and competent cyprid of Balanus amphitrite were added. After 24 hours, the number of attached cyprids in each dish was determined, and normalized to the number added initially. Ten replicate dishes were analyzed for each concentration.

EXAMPLE III

Synthesis of subspecimen 1 was as follows: $ClSO_3H$ (0.2 ml) was added dropwise to 2 (200 mg) in pyridine (0.5 ml) with stirring at 20°. Ice water was added, and the acidic aqueous mixture was extracted with $Et_2O$, basified, extracted with $Et_2O$, and $H_2O$ removed under vacuum. Residue was triturated with $H_2O$, neutralized, dried under vacuum, and triturated with MeOH. MeOH soluble residue purified by HPLC gave 187 mg for subspecimen 1 (63%). Similar yields obtained for other analogs

EXAMPLE IV

All mass spectra were negative HRFAB. The matrix used was thiglycerol/glycerol. NMR * assignments interchangeable.

Zosteric acid from Example III: $[M-1]^-$ 242.9963, $C_9H_7O_6S$, $\Delta 0.0$ mmu. APT and $^{13}C$ NMR (62.5 MHz, $CD_3OD$-$D_2O$) : $\delta 176.5$ (s, C–1), 153.5 (s, C–7), 140.8 (d, C–3), 134.3 (s, C–4), 130.2 (2C, d, *C–5), 125.8 (d, C–2), 122.9 (2C, d, *C–6). $^1H$ NMR (300 MHz, $CD_3OD$-$D_2O$): $\delta 7.59$ (2H, d, J=8.7 Hz, *H–5), 7.34 (1H, d, J=16.2 Hz, H–3), 7.27 (2H, d, J=8.4 Hz, *H–6), 6.44 (1H, d, J=16.2 Hz, H–2).

Zosteric acid methyl ester: $[M-1]^-$ 257.0118, $C_{10}H_9O_6S$, $\Delta 0.2$ mmu of calculated. $^{13}C$ NMR (75 MHz, $CD_3OD$) : $\delta 167.8$, 154.5, 144.3, 130.7, 128.9 (2C), 121.2 (2C), 116.5, 50.8. $^1H$ NMR (300 MHz, $CD_3OD$): $\delta 7.65$ (d, J=15.9 Hz), 7.57 (d, J=8.7 Hz), 7.31 (d, J=8.7 Hz), 6.45 (d, J=15.9 Hz), 3.72 (s).

Synthetic version of subspecimen 1: $[M-1]^-$ 242.9958, $C_9H_7O_6S$, $\Delta 0.5$ mmu of calculated. NMR spectra same as zosteric acid.

EXAMPLE V

Mass spectra for another analog of subspecimen 1: $[M-2H+Na]^-$ 360.9285, $C_9H_6NaO_{10}S_2$, $\Delta 1.5$ mmu of calculated. $^{13}C$ NMR (62.5 MHz, $D_2O$) : $\delta 176.5$, 144.9, 144.3, 140.3, 135.3, 127.4, 124.4, 123.3, 123.1. $^1H$ NMR (250 MHz, $D_2O$): $\delta 7.81$ (br s), 7.62 (br s), 7.45 (d, J=16.0 Hz), 6.61 (d, J=16.0 Hz). The matrix used was glycerol only.

EXAMPLE VI

Mass spectra for subspecimens 6 and 7 mixture: $[M-1]^-$ 258.9888, $C_9H_7O_7S$, $\Delta 2.4$ mmu of calculated. $^{13}C$ NMR (62.5 MHz, $D_2O$) : $\delta 177.0$, 176.7, 151.0, 149.4, 141.2, 140.9, 140.1, 135.4, 128.9, 128.1, 127.2, 125.7, 124.1, 123.5, 123.0, 121.4, 118.8, 117.0. $^1H$ NMR (250 MHz, $D_2O$): $\delta 7.74$ (s), 7.59 (d, J=2.0 Hz), 7.56 (s), 7.42–7.35 (m), 7.30 (d, J=3.2 Hz), 7.22 (d, J=1.9 Hz), 7.18 (d, J=2.0 Hz), 7.15 (d, J=2.0 Hz), 7.03 (d, J=8.4 Hz), 6.53 (d, J=18.3 Hz), 6.41 (d, J=14.8 Hz). The matrix used was only glycerol.

Another analog subspecimen: $[M-1]^-$ 273.0083, $C_{10}H_9O_7S$, $\Delta 1.4$ mmu of calculated. $^{13}C$ NMR (62.5 MHz, $CD_3OD$) : $\delta 175.6$, 153.1, 143.5, 140.2, 134.8, 126.3, 123.5, 121.2, 112.5, 56.6. $^1H$ NMR (250 MHz, $CD_3OD$): $\delta 7.40$ (d, J=8.3 Hz), 7.30 (d, J=15.9 Hz), 7.14 (d, J=1.9 Hz), 7.02 (dd, J=8.4, 1.9 Hz), 6.40 (d, J=15.9 Hz), 3.83 (s).

What is claimed is:

1. A method of using a sulfooxyphenylcarboxylic acid to protect against biofouling accumulation on an artificial surface, comprising:
    (a) providing an antifouling composition comprising a sulfooxyphenylcarboxylic acid; and
    (b) applying said antifouling composition to said artificial surface.

2. The method as defined in claim 1 wherein said antifouling composition comprises a sulfate ester of cinnamic acid.

3. The method as defined in claim 2 wherein said antifouling composition comprises p-sulfooxy cinnamic acid.

4. The method as defined in claim 2 wherein said antifouling composition comprises a femlic acid sulfate.

5. A method of using a sulfooxyphenylcarboxylic acid to protect against biofouling accumulation on an artificial surface, comprising:
    (a) providing an antifouling composition comprising a sulfooxyphenylcarboxylic acid;
    (b) dissolving said antifouling composition to form a solution; and
    (c) contacting said antifouling compound with said artificial surface.

6. The method as defined in claim 5 wherein said sulfooxyphenylcarboxylic acid is selected from the group consisting of p-sulfooxy cinnamic acid, p-sulfooxy ferulic acid, m,p-disulfooxy caffeic acid, p-sulfooxy benzoic acid, p-sulfooxy vanillic acid, 2,5-disulfooxy gentissic acid, p-sulfooxy gallic acid and p-sulfooxy protocatechuic acid.

7. An article of manufacture resistant to marine biofouling, comprising:
    (a) an artificial surface; and
    (b) an antifouling composition contacting said surface, said composition comprising a sulfooxyphenylcarboxylic acid.

8. The article as defined in claim 7 wherein said sulfooxyphenylcarboxylic acid is a sulfate ester of cinnamic acid.

9. The article as defined in claim 7 wherein said sulfooxyphenylcarboxylic acid is selected from the group consisting of p-sulfooxy cinnamic acid, p-sulfooxy ferulic acid, m,p-disulfooxy caffeic acid, p-sulfooxy benzoic acid, p-sulfooxy vanillic acid, 2,5-disulfooxy gentissic acid, p-sulfooxy gallic acid and p-sulfooxy protocatechuic acid.

10. The article as defined in claim 9 wherein said sulfooxyphenylcarboxylic acid is p-sulfooxy cinnamic acid.

* * * * *